United States Patent [19]
Hwang et al.

[11] Patent Number: 5,112,292
[45] Date of Patent: May 12, 1992

[54] HELIFOIL PUMP

[75] Inventors: Ned H. C. Hwang, Houston; David P. Summers, Montgomery, both of Tex.

[73] Assignee: American Biomed, Inc., The Woodlands, Tex. ; a part interest

[21] Appl. No.: 603,160

[22] Filed: Oct. 25, 1990

Related U.S. Application Data

[62] Division of Ser. No. 295,234, Jan. 9, 1989, Pat. No. 4,969,865.

[51] Int. Cl.⁵ .............................................. A61F 1/24
[52] U.S. Cl. .......................................... 600/16; 623/3; 601/181; 418/900
[58] Field of Search .............. 606/16; 673/3; 415/900; 418/220, 201; 416/63, 223 R, 235, 237, 19, 603, 228, 176; 604/151

[56] References Cited

U.S. PATENT DOCUMENTS

| | | |
|---|---|---|
| 3,382,199 | 5/1983 | Isaacson . |
| 3,487,789 | 1/1970 | Rafferty et al. ...................... 415/900 |
| 3,505,987 | 4/1978 | Heilman . |
| 3,667,069 | 6/1972 | Blackshear et al. . |
| 3,995,617 | 12/1976 | Watkins et al. . |
| 4,051,840 | 10/1977 | Kantrowitz et al. . |
| 4,102,610 | 7/1978 | Taboada et al. . |
| 4,173,796 | 11/1979 | Jarvik . |
| 4,275,988 | 6/1981 | Kalashnikov et al. ............... 416/416 |
| 4,279,614 | 7/1981 | Moise ..................... 600/16 |
| 4,625,712 | 12/1986 | Wampler . |
| 4,753,221 | 6/1988 | Kensey et al. ...................... 604/151 |
| 4,817,586 | 4/1989 | Wampler . |
| 4,846,152 | 7/1989 | Wampler et al. ...................... 600/16 |
| 4,861,330 | 8/1989 | Voss ...................... 600/18 |

FOREIGN PATENT DOCUMENTS 21847185A 7/1987 United Kingdom .

OTHER PUBLICATIONS

"Tiny Pump Gives Heart a Big Rest", Henig, Washington Post, Jan. 31, 1989, 1 pg.
"A Pump for Extracorporeal Circulation", Medical Societies—Feb. 14, 1959.

Primary Examiner—Randy C. Shay
Assistant Examiner—K. M. Reiche
Attorney, Agent, or Firm—Gunn, Lee & Miller

[57] ABSTRACT

A temporary circulatory assist pump is disclosed for implantation in the heart of a patient through the femoral artery. The pump is driven by a flexible drive shaft extending through a catheter and being connected to a power source outside the body of the patient. The pump utilizes a helical-shaped foil impeller to pump blood at a rate of approximately three to four liters per minute through the circulatory system of the patient.

3 Claims, 2 Drawing Sheets

HELIFOIL PUMP

This is a divisional of application Ser. No. 07/295,234 filed Jan. 9, 1989, now U.S. Pat. No. 4,969,865.

BACKGROUND OF THE DISCLOSURE

This invention relates to blood pumps, particularly a temporary circulatory assist pump adapted for insertion into the vascular system of a patient to provide temporary circulatory assistance for a dyskinetic left or right ventricle of the heart.

Death and disability from heart disease are most commonly due to the pumping inadequacy of an infarcted left or right ventricle. The heart of a patient suffering from this condition functions in many other respects but does not provide sufficient blood flow to keep the patient alive. Typically, a patient suffering from this condition would require major surgery to maintain the heart and provide sufficient blood flow for the patient.

Another area where temporary circulatory assistance may be required is in allograft cardiac replacement or heart transplants. Although one year survivals after a heart transplant now approach 80%, a great many patients die waiting for a transplant, as do many of the 20% who might be saved by circulatory assistance while immunosuppressive agents are combatting the body's natural rejection response of a transplanted heart. There is a great need for an effective circulatory assist pump for maintaining the life of a patient until the transplant can be accomplished and the allograft is stabilized. As the average life expectancy of the U.S. population continues to increase, coronary artery disease and chronic congestive heart failure can be expected to significantly increase the utilization of mechanical circulatory assistance. A realistic estimate of the number of potential candidates for mechanical circulatory assistance would be approximately 300,000 patients each year in the U.S. This number will grow at a rate of 6% per year until the population of "baby boomers" peaks around the year 2020.

Methods and apparatus exist in the prior art for circulatory assistance of a heart. In U.S. Pat. No. 4,625,712 a high capacity intravascular blood pump is disclosed. The pump in inserted into the heart through the femoral artery and driven via a flexible cable from an external power source. The drive cable is contained within a catheter attached to the pump. The pump is rotated in the range of 10,000–20,000 rpm to produce blood flow on the order of 4 liters per minute.

U.S. Pat. No. 3,505,987 discloses a counterpulsation system for aiding coronary circulation. The system includes an expandable impeller located within the aorta of a patient. The impeller is expanded and contracted while simultaneously being reciprocated within the aorta and synchronized with the pumping activity of the heart for reducing aortic pressure during systole and increasing aortic pressure during diastole.

U.S. Pat. No. 3,667,069 discloses an implantable jet pump for replacing or assisting the right heart. The jet pump comprises an elongated tubular structure including an upstream driving nozzle from which a driving flow of arterial blood under pressure is ejected into a suction nozzle creating its own reduced pressure to cause venous blood to be sucked into and admixed with the driving flow for distribution to the pulmonary circulation system. The jet pump may be powered by blood pumped from the left heart or an artificial replacement for the left heart.

U.S. Pat. No. 4,051,840 discloses an aortic patch which may be surgically implanted in the thoracic aorta. The aortic patch is systematically inflated and deflated to generate pressure waves in the blood stream. The pressure waves assist the heart by augmenting the circulation of the blood to the body.

Generally, the methods available for circulatory assistance of the heart require major surgery for the implantation of the device which presents a great risk to the survival of the patient. The device disclosed in U.S. Pat. No. 4,625,712 may be introduced into the heart through the iliofemoral artery thus avoiding major surgery and reducing the risk to the patient. However, adequate blood flow requires that the pump and drive shaft be rotated at extremely high rpm through the bends and sharp curves of the iliofemoral and aortic arteries and therefore, extreme care must be taken to avoid creation of hot spots in the arteries.

Another disadvantage associated with high rpm blood pumps is the high risk of damaging a substantial percentage of the blood cells of the blood. Damaged blood cells are expelled by the body and new blood cells must be generated to replace them. This may create additional strain on the system of a patient who is already in critical condition. The prior art has thus been unable to provide an easily implanted low risk temporary circulatory assist pump capable of providing sufficient blood flow to assist a heart so that the heart may heal itself or keep the patient alive while waiting for a transplant to become available.

SUMMARY OF THE INVENTION

The present invention is directed to a miniature temporary circulatory assist pump adapted to be inserted in the heart of the patient for circulatory assistance. The pump in a preferred embodiment is introduced into the left ventricle of the heart by a catheter passed through the arterial system of the patient. The pump utilizes a helical-shaped foil impeller housed within a cylindrical housing to deliver large volumes of blood at relatively low rpm within a nominal physiological pressure.

DETAILED DESCRIPTION OF THE DRAWINGS

So that the manner in which the above recited features, advantages and objects of the present invention are attained and can be understood in detail, more particular description of the invention, briefly summarized above, may be had by reference to the embodiments thereof which are illustrated in the appended drawings.

It is to be noted, however, that the appended drawings illustrate only typical embodiments of this invention and are therefore not to be considered limiting of its scope, for the invention may admit to other equally effective embodiments.

DETAILED DESCRIPTION OF THE PREFERRED EMBODIMENT

Figure 2:
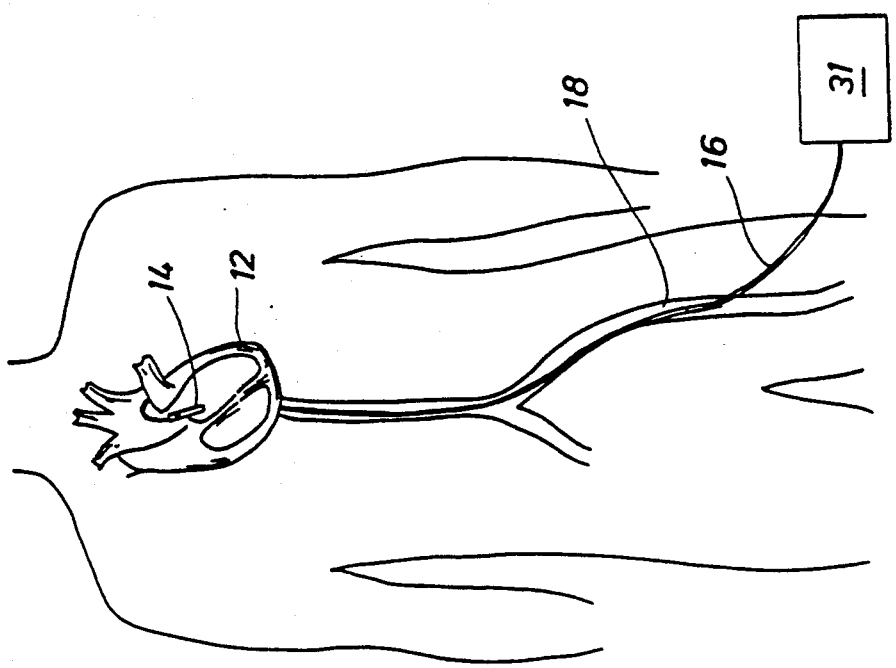
FIG. 2 is a schematic view illustrating the insertion of the pump of the invention through the femoral artery of a patient.
Figure 1:
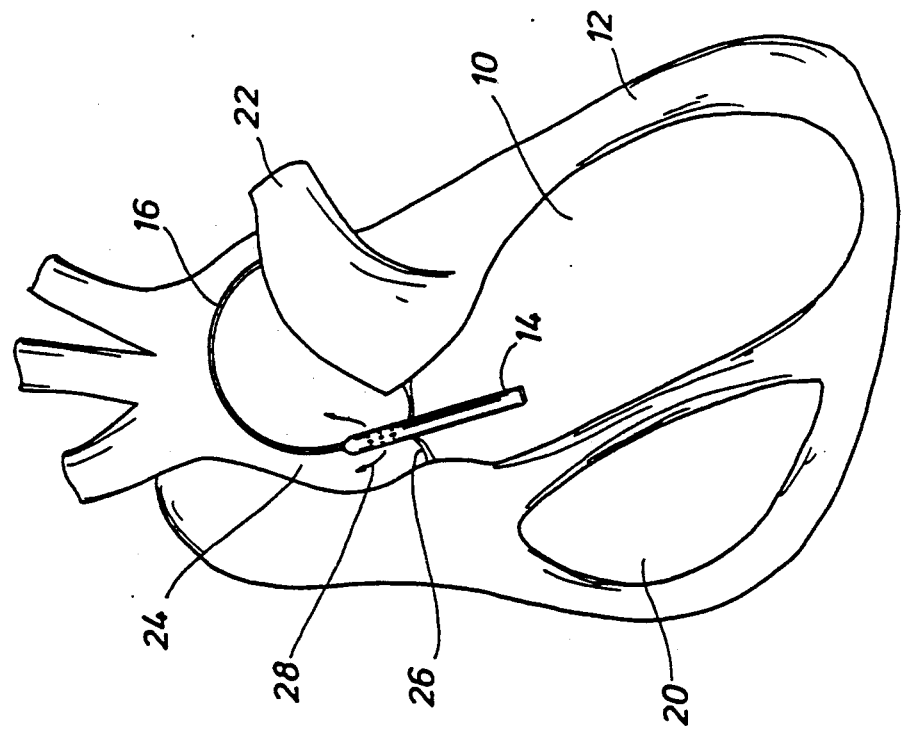
FIG. 1 is an illustrative view of a section of a human heart depicting the preferred position of the pump of the invention in the left ventricle of the heart.

Referring first to FIGS. 1 and 2 of the drawings, the blood pump of the invention is shown inserted in the left ventricle 10 of the heart 12. The blood pump is generally identified by the reference numeral 14 and is carried at the forward end of a catheter 16. Access to the heart 12 is provided in the preferred embodiment through the femoral artery 18. This is the preferred insertion point, however, it is understood that the heart 12 may be accessed through other arteries or other surgical means. In the preferred embodiment, the blood pump 14 is located in the left ventricle 10. However, in some circumstances it may be desirable to locate the blood pump 14 in the right ventricle 20. Access to the right ventricle 20 may be provided through the pulmonary artery 22. In operation, the intake end of the blood pump 14 shown in FIG. 1 is located within the left ventricle 10. The outlet or discharge end of the blood pump 14 is located in the aorta 24. The blood pump 14 thus extends partially into the left ventricle 10 through the heart valve 26. Blood is pumped through the blood pump 14 from the left ventricle 10 in the direction of the arrows 28 into the aorta 24.

Figure 3:
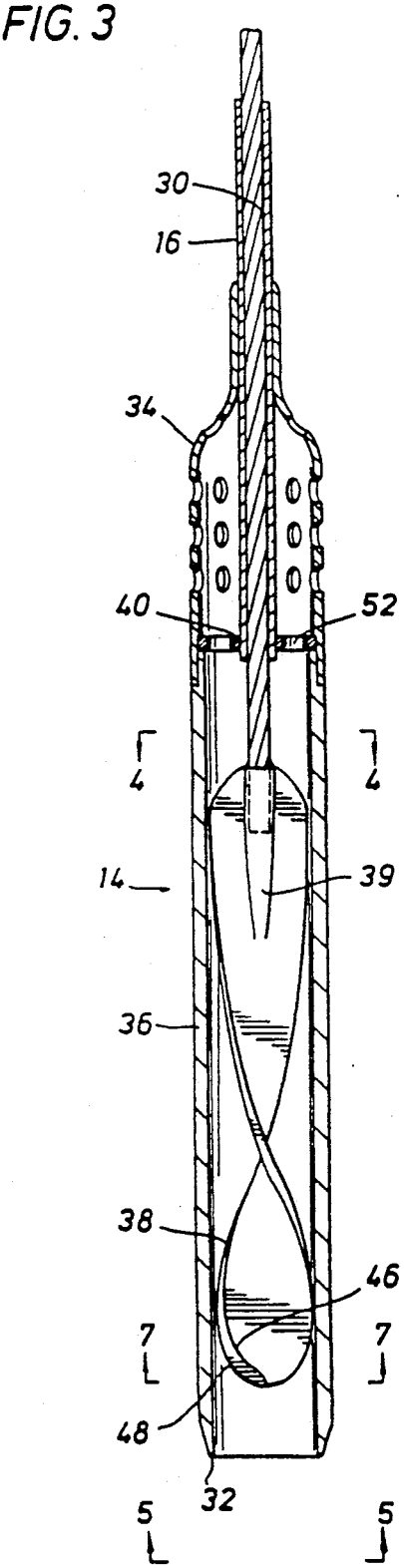
FIG. 3 is a partial sectional view of the pump of the invention.

Referring now to FIG. 3, the pump 14 is shown in greater detail. The pump 14 is driven by a flexible drive shaft 30 which extends through the catheter 16. The drive shaft 30 is driven by a motor 31 located outside the patient's body, as best shown in FIG. 2. The pump 14 is secured to the distal end of the catheter 16. The pump 14 and catheter 16 are guided through the femoral artery to the left ventricle 10. When the left ventricle 10 is reached, the pump 14 is positioned in the left ventricle 10 of the heart. Utilizing known insertion techniques, the pump 14 is positioned so that the intake end 32 extends through the heart valve 26 into the left ventricle 10. The discharge end 34 of the pump 14 is positioned outside the left ventricle 10 so that pumped blood is discharged into the aorta 24 as shown in FIG. 1.

In the embodiment of the invention shown in FIG. 3, the pump 14 comprises a substantially cylindrical elongate housing 36. The intake end 32 of the housing 36 is blunted so that it may be easily inserted into the left ventricle 10 past the heart valve 26 without damaging the heart valve or any of the heart tissue. The intake end 32 is open so that blood collected in the left ventricle 10 may flow freely into the pump 14. Housed within the housing 36 is a helical-shaped foil impeller 38. The impeller 38 is connected to the drive shaft 30. The drive shaft 30 is centrally positioned within the discharge end 34 of the housing 36 by a shaft stabilizer 40.

In the preferred embodiment as shown in FIG. 1, the pump 14 is positioned in the left ventricle 10 of the heart 12 and blood from the left ventricle 10 is pumped into the aorta 24 upon rotation of the impeller 38. The impeller 38 functions in much the same fashion as an airfoil moving through a liquid medium. Blasius' first equation of fluid forces on a body in motion describes forces on a submerged body. The forces may be resolved into components in directions perpendicular to the motion (Y-axis) and parallel to the motion (X-axis). These forces are known as "lift" and "drag" respectively. In fluid mechanics, lift and drag are equal to the component of thrust. Rotation of the helical-shaped foil impeller 38 within the cylindrical housing 36 produces characteristics similar to the lift and drag forces produced by an airflow. That is, both high and low pressure forces are produced on either side of the rotating helical impeller 38 within the cylinder 36 which produces a thrust force to energize fluid motion within the cylinder 36.

Figure 6:
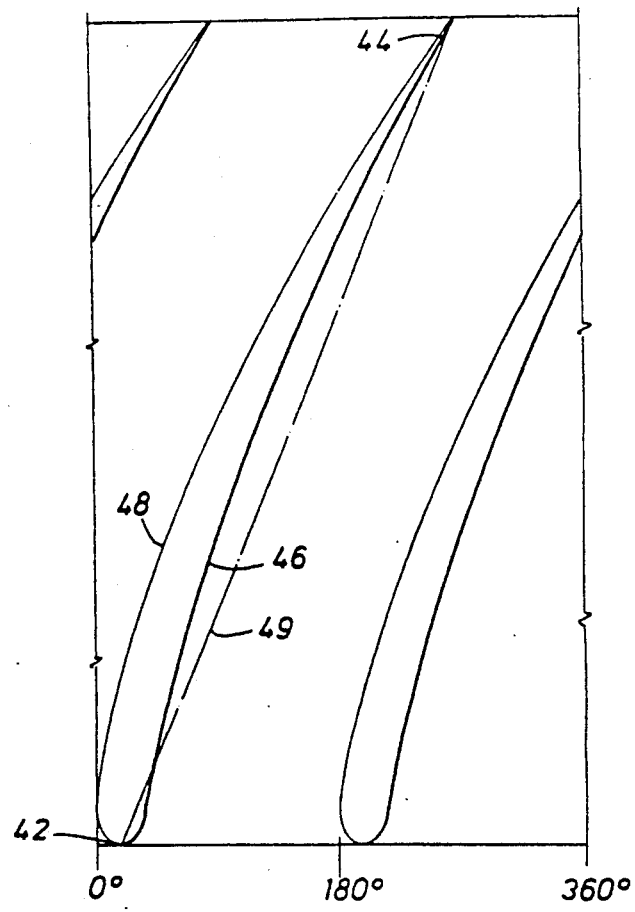
FIG. 6 is an illustrative view of of the helical-shaped foil impeller of the invention depicted in a two dimensional plane.
Figure 7:
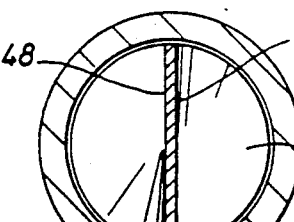
FIG. 7 is a sectional view of the pump of the invention taken along lines 7—7 of FIG. 3.

Referring now to FIG. 6, impeller 38 is shown in a two dimensional plane. It will be observed that the profile of the impeller 38 is similar to that of an airfoil and includes a forward or leading end 42 and a trailing end 44. The impeller 38 tapers from the leading end 42 to the trailing end 44. As the impeller 38 is rotated, high and low pressure forces are created on either side of the rotating impeller. The high pressure side is defined by the surface 46 and the low pressure side is defined by the surface 48. The cord line 49 defines the angle of attack of the impeller 38 which is optimized to provide maximum flow rate at the physiological pressure level.

Figure 5:
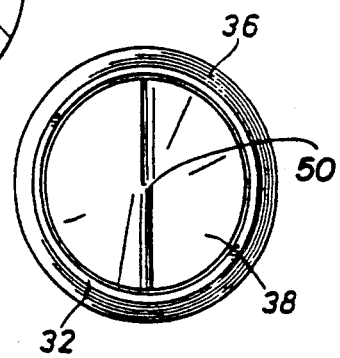
FIG. 5 is a sectional view of the pump of the invention taken along line 5—5 of FIG. 3.
Figure 4:
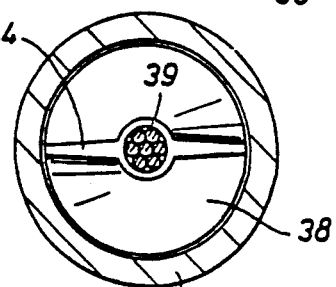
FIG. 4 is a sectional view of the pump of the invention taken along line 4—4 of FIG. 3.

Referring now to FIG. 3, it will be observed that the impeller 38 is wrapped or twisted to form a helical profile. The forward end of the impeller 38 as best shown in FIG. 5 presents a leading edge 50 which extends across the housing 36. From the leading edge 50, the impeller 38 defines a continuous contour to the trailing end 44 as shown in FIG. 4. The contour defines a continuous rotating passage for transforming the blood flow from a simple mass displacement at the inlet 32 to transformational blood flow producing a thrust and a streamline shape at the discharge end 34 of the pump 14. The transformational flow may be calculated and graphically described utilizing the Joukowsky transformation. Thus, the Joukowsky transformation may be used to calculate the thrust generated by the rotational motion of the impeller 38 within the housing 36. The rotational motion of the impeller 38 creates a thrust force which draws blood into the cylindrical housing 36 and discharges the blood through apertures 52 extending through the shaft stabilizer 40 and through ports in the discharge end 34 into the aorta 24 for circulation through the patient's vascular system. The trailing end 44 of the impeller 38 is enlarged slightly at the central portion thereof for connection to the drive shaft 30. The enlarged portion 39 however tapers outwardly to the trailing end 44 of the impeller 38 such that it does not interfere with the blood flow to the discharge end 34 of the housing 36.

The helical-shaped foil profile of the impeller 38 is designed to maximize blood flow through the housing 36 while minimizing the potential damage to blood cells. The impeller 38 is rotated in the range of 6,000 to 10,000 rpm to produce a blood flow of approximately 3 to 4 liters per minute. Turbulence however is minimized by the continuous contour of the flow passage defined by the impeller 38. The thrust generated by the high pressure side of the impeller 38 draws the blood through the pump 14 while minimizing the turbulence in the blood flow. The impeller 38 cooperates with the cylindrical housing 36 to form a continuous, smooth, rotating passage to transform the blood flow from a simple mass displacement at the inlet end 32 of the pump 14 to a transformational flow at the trailing end 44 of the impeller 38. In this manner, trauma to the blood cells is minimized, yet sufficient blood flow is developed to sustain the patient.

While the foregoing is directed to the preferred embodiment of the present invention, other and further embodiments of the invention may be devised without departing from the basic scope thereof, and the scope thereof is determined by the claims which follow.

WHAT IS CLAIMED IS:

1. A method of temporarily providing circulatory assistance to the heart of a patient, comprising the steps of:

(a) positioning a pump carried by a catheter in the vascular system of a patient, said pump having intake port means at an intake end thereof, discharge port means at an opposite end thereof and a continuous rotating passage, said positioning step including inserting the intake port means of said pump into the heart of the patient and the discharge port means in the vascular system of the patient downstream of the heart.

(b) creating a pressure differential in the pump for maximizing blood flow through the pump at a physiological pressure level; and (c) pumping blood from the intake port means to the discharge port means through the continuous rotating passage within the pump transforming mass displacement at the intake port means into transformational blood flow at the discharge port means.

2. The method of claim 1 wherein the pump further includes an impeller coaxially located therewithin which defines the passage and wherein the step of pumping further includes minimizing turbulence by flowing the blood through the continuous, rotating passage.

3. The method of claim 1 wherein the step of inserting includes inserting the intake port means in the left ventricle of the patient's heart and the discharge port means in the patient÷s aortic arch.

* * * * *